United States Patent
Rao et al.

(10) Patent No.: US 11,638,638 B2
(45) Date of Patent: May 2, 2023

(54) FILLING STRUCTURE FOR A GRAFT SYSTEM AND METHODS OF USE

(71) Applicant: Endologix LLC, Irvine, CA (US)

(72) Inventors: K. T. Venkateswara Rao, San Jose, CA (US); Raj P. Ganpath, Mountain View, CA (US); Amy Lee, Sunnyvale, CA (US); Anupama Karwa, San Francisco, CA (US)

(73) Assignee: Endologix LLC, Irvine, CA (US)

( * ) Notice: Subject to any disclaimer, the term of this patent is extended or adjusted under 35 U.S.C. 154(b) by 355 days.

(21) Appl. No.: 16/382,118

(22) Filed: Apr. 11, 2019

(65) Prior Publication Data

US 2019/0231515 A1 Aug. 1, 2019

Related U.S. Application Data

(63) Continuation of application No. 12/966,852, filed on Dec. 13, 2010, now abandoned.

(60) Provisional application No. 61/291,279, filed on Dec. 30, 2009.

(51) Int. Cl.
*A61F 2/07* (2013.01)
*A61F 2/90* (2013.01)

(52) U.S. Cl.
CPC .................. *A61F 2/07* (2013.01); *A61F 2/90* (2013.01); *A61F 2002/075* (2013.01); *A61F 2002/077* (2013.01); *A61F 2230/0008* (2013.01); *A61F 2230/0067* (2013.01)

(58) Field of Classification Search
CPC ................................................ A61F 2002/077
See application file for complete search history.

(56) References Cited

U.S. PATENT DOCUMENTS

| 4,130,904 A | * | 12/1978 | Whalen | A61F 2/06 138/122 |
|---|---|---|---|---|
| 4,565,733 A | | 1/1986 | Purdy | |
| 4,638,803 A | | 1/1987 | Rand | |
| 4,641,653 A | | 2/1987 | Rockey | |
| 4,704,126 A | | 11/1987 | Baswell | |
| 4,710,192 A | | 12/1987 | Liotta | |
| 4,728,328 A | | 3/1988 | Hughes et al. | |

(Continued)

FOREIGN PATENT DOCUMENTS

| CN | 1174016 A | 2/1998 |
|---|---|---|
| DE | 4010975 A1 | 10/1991 |

(Continued)

OTHER PUBLICATIONS

US 5,824,035 A, 10/1998, Lauterjung (withdrawn)

(Continued)

*Primary Examiner* — Martin T Ton
(74) *Attorney, Agent, or Firm* — Foley & Lardner LLP

(57) ABSTRACT

A system for treating an aneurysm includes a first double-walled filling structure having an outer wall and an inner wall. The filling structure is adapted to be filled with a hardenable fluid filling medium so that the outer wall conforms to an inside surface of the aneurysm and the inner wall forms a generally tubular lumen to permit blood flow therethrough. The inner wall comprises a blood contacting layer and a reinforcing layer. The reinforcing layer prevents circumferential creep or elastic expansion of the lumen.

14 Claims, 8 Drawing Sheets

Section A-A

(56) References Cited

U.S. PATENT DOCUMENTS

| | | |
|---|---|---|
| 4,731,073 A | 3/1988 | Robinson |
| 4,733,665 A | 3/1988 | Palmaz |
| 4,743,258 A | 5/1988 | Ikada |
| 4,763,654 A | 8/1988 | Jang |
| 4,856,516 A | 8/1989 | Hillstead |
| 4,858,264 A | 8/1989 | Reinhart |
| 4,892,544 A | 1/1990 | Frisch |
| 4,936,057 A | 6/1990 | Rhoades |
| 4,976,692 A | 12/1990 | Atad |
| 5,002,532 A | 3/1991 | Gaiser |
| 5,074,845 A | 12/1991 | Miraki |
| 5,104,404 A | 4/1992 | Wolff |
| 5,108,417 A | 4/1992 | Sawyer |
| 5,122,154 A | 6/1992 | Rhodes |
| 5,133,732 A | 7/1992 | Wiktor |
| 5,139,480 A | 8/1992 | Hickle |
| 5,156,620 A | 10/1992 | Pigott |
| 5,195,984 A | 3/1993 | Schatz |
| 5,199,226 A | 4/1993 | Rose |
| 5,217,484 A | 6/1993 | Marks |
| 5,222,970 A | 6/1993 | Reeves |
| 5,234,437 A | 8/1993 | Sepelka |
| 5,236,447 A * | 8/1993 | Kubo ................. A61L 27/14 623/1.13 |
| 5,242,399 A | 9/1993 | Lau |
| 5,250,071 A | 10/1993 | Palermo |
| 5,261,916 A | 11/1993 | Engelson |
| 5,263,964 A | 11/1993 | Purdy |
| 5,292,331 A | 3/1994 | Houki et al. |
| 5,314,444 A | 5/1994 | Gianturco |
| 5,330,520 A | 5/1994 | Palmaz et al. |
| 5,330,528 A * | 7/1994 | Lazim ................. A61F 2/07 606/194 |
| 5,334,217 A | 8/1994 | Das |
| 5,350,397 A | 9/1994 | Palermo |
| 5,352,199 A | 10/1994 | Tower |
| 5,375,612 A | 12/1994 | Cottenceau |
| 5,383,892 A | 1/1995 | Cardon |
| 5,421,955 A | 6/1995 | Lau |
| 5,423,849 A | 6/1995 | Engelson |
| 5,425,739 A | 6/1995 | Jessen |
| 5,425,744 A | 6/1995 | Fagan |
| 5,441,510 A | 8/1995 | Simpson |
| 5,441,515 A | 8/1995 | Khosravi |
| 5,443,477 A | 8/1995 | Marin |
| 5,443,496 A | 8/1995 | Schwartz |
| 5,449,373 A | 9/1995 | Pinchasik |
| 5,485,667 A | 1/1996 | Kleshinski |
| 5,507,769 A | 2/1996 | Lane |
| 5,496,277 A | 3/1996 | Termin |
| 5,507,767 A | 4/1996 | Maeda |
| 5,507,771 A | 4/1996 | Gianturco |
| 5,514,115 A | 5/1996 | Frantzen |
| 5,514,154 A | 5/1996 | Lau |
| 5,522,882 A | 6/1996 | Gaterud |
| 5,530,528 A | 6/1996 | Houki et al. |
| 5,531,741 A | 7/1996 | Barbacci |
| 5,534,024 A | 7/1996 | Rogers et al. |
| 5,545,210 A | 8/1996 | Hess et al. |
| 5,549,662 A | 8/1996 | Fordenbacher |
| 5,549,663 A | 8/1996 | Cottone, Jr. |
| 5,554,181 A | 9/1996 | Das |
| 5,562,641 A | 10/1996 | Flomenblit |
| 5,562,698 A | 10/1996 | Parker |
| 5,562,728 A | 10/1996 | Lazarus |
| 5,569,295 A | 10/1996 | Lam |
| 5,578,074 A | 11/1996 | Mirigian |
| 5,578,149 A | 11/1996 | De Scheerder |
| 5,591,195 A | 1/1997 | Taheri |
| 5,591,223 A | 1/1997 | Lock |
| 5,591,226 A | 1/1997 | Trerotola |
| 5,591,228 A | 1/1997 | Edoga |
| 5,591,230 A | 1/1997 | Horn |
| 5,593,417 A | 1/1997 | Rhodes |
| 5,601,600 A | 2/1997 | Ton |
| 5,603,721 A | 2/1997 | Lau |
| 5,605,530 A | 2/1997 | Fischell |
| 5,607,442 A | 3/1997 | Fischell |
| 5,607,445 A | 3/1997 | Summers |
| 5,607,468 A | 3/1997 | Rogers |
| 5,609,605 A | 3/1997 | Marshall |
| 5,617,878 A | 4/1997 | Taheri |
| 5,618,299 A | 4/1997 | Khosravi |
| 5,624,411 A | 4/1997 | Tuch |
| 5,630,840 A | 5/1997 | Mayer |
| 5,632,760 A | 5/1997 | Sheiban |
| 5,632,762 A | 5/1997 | Myler |
| 5,632,763 A | 5/1997 | Glastra |
| 5,632,771 A | 5/1997 | Boatman |
| D380,266 S | 6/1997 | Boatman |
| 5,634,941 A | 6/1997 | Winston |
| 5,636,641 A | 6/1997 | Fariabi |
| D380,831 S | 7/1997 | Kavteladze |
| 5,662,614 A | 9/1997 | Edoga |
| 5,665,117 A | 9/1997 | Rhodes |
| 5,674,241 A | 10/1997 | Bley |
| 5,676,697 A | 10/1997 | McDonald |
| 5,683,449 A | 11/1997 | Marcade |
| 5,690,643 A | 11/1997 | WiJay |
| 5,693,038 A | 12/1997 | Suzuki et al. |
| 5,693,067 A | 12/1997 | Purdy |
| 5,693,088 A | 12/1997 | Lazarus |
| 5,697,971 A | 12/1997 | Fischell |
| 5,709,707 A | 1/1998 | Lock |
| 5,718,713 A | 2/1998 | Frantzen |
| 5,723,004 A | 3/1998 | Dereurne |
| 5,725,568 A | 3/1998 | Hastings |
| 5,725,572 A | 3/1998 | Lam |
| 5,728,068 A | 3/1998 | Leone |
| 5,728,131 A | 3/1998 | Frantzen |
| 5,728,158 A | 3/1998 | Lau |
| 5,733,303 A | 3/1998 | Israel et al. |
| 5,735,892 A | 4/1998 | Myers |
| 5,735,893 A | 4/1998 | Lau |
| 5,741,327 A | 4/1998 | Frantzen |
| 5,741,333 A | 4/1998 | Frid |
| 5,746,691 A | 5/1998 | Frantzen |
| 5,755,769 A | 5/1998 | Richard |
| 5,755,773 A | 5/1998 | Evans et al. |
| 5,755,778 A | 5/1998 | Kleshinski |
| 5,766,151 A | 6/1998 | Valley et al. |
| 5,766,238 A | 6/1998 | Lau |
| 5,769,882 A | 6/1998 | Fogarty et al. |
| 5,776,114 A | 7/1998 | Frantzen |
| 5,776,161 A | 7/1998 | Globerman |
| 5,782,907 A | 7/1998 | Frantzen |
| 5,785,679 A | 7/1998 | Abolfathi et al. |
| 5,788,626 A | 8/1998 | Thompson |
| 5,797,953 A | 8/1998 | Tekulve |
| 5,800,393 A | 9/1998 | Sahota |
| 5,800,512 A | 9/1998 | Lentz et al. |
| 5,800,514 A | 9/1998 | Nunez |
| 5,800,525 A | 9/1998 | Bachinski |
| 5,807,404 A | 9/1998 | Richter |
| 5,810,872 A | 9/1998 | Kanesaka |
| 5,824,037 A | 10/1998 | Fogarty et al. |
| 5,824,040 A | 10/1998 | Cox |
| 5,824,049 A | 10/1998 | Ragheb |
| 5,824,054 A | 10/1998 | Khosravi et al. |
| 5,824,056 A | 10/1998 | Rosenberg |
| 5,827,321 A | 10/1998 | Roubin |
| 5,836,966 A | 11/1998 | St. Germain |
| 5,843,160 A | 12/1998 | Rhodes |
| 5,843,175 A | 12/1998 | Frantzen |
| 5,846,246 A | 12/1998 | Dirks |
| 5,846,261 A | 12/1998 | Kotula et al. |
| 5,849,037 A | 12/1998 | Frid |
| 5,860,998 A | 1/1999 | Robinson |
| 5,863,627 A | 1/1999 | Szycher |
| 5,867,762 A | 2/1999 | Rafferty et al. |
| 5,868,685 A | 2/1999 | Powell et al. |
| 5,868,708 A | 2/1999 | Hart |
| 5,868,782 A | 2/1999 | Frantzen |
| 5,871,537 A | 2/1999 | Holman et al. |

(56) References Cited

U.S. PATENT DOCUMENTS

| | | |
|---|---|---|
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A | 5/1999 | Schatz |
| 5,919,224 A | 7/1999 | Thompson |
| 5,928,279 A | 7/1999 | Shannon et al. |
| 5,931,866 A | 8/1999 | Frantzen |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,190,406 B1 | 2/2001 | Horton et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 | 5/2001 | Khosravi et al. |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 | 9/2001 | Solovay et al. |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 | 5/2002 | Chobotov |
| 6,409,757 B1 | 6/2002 | Trout, III et al. |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujaweki |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 6,969,373 B2 | 11/2005 | Schwartz et al. |
| 7,022,100 B1 | 4/2006 | Aboul-Hosn et al. |
| 7,105,012 B2 | 9/2006 | Trout, III |
| 7,112,217 B1 | 9/2006 | Kugler |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | Depalrna et al. |
| 7,435,253 B1 | 10/2008 | Hartley et al. |
| 7,530,988 B2 | 5/2009 | Evans et al. |
| 7,666,220 B2 | 2/2010 | Evans et al. |
| 7,682,383 B2 | 3/2010 | Robin |
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,951,448 B2 | 5/2011 | Lee et al. |
| 8,133,559 B2 | 3/2012 | Lee et al. |
| 8,801,768 B2 | 8/2014 | Karwa et al. |
| 2001/0020184 A1 | 9/2001 | Dehdashttan et al. |
| 2001/0027337 A1 | 10/2001 | Robin |
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0014075 A1 | 1/2003 | Rosenbluth et al. |
| 2003/0028209 A1 | 2/2003 | Teoh et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0220649 A1 | 11/2003 | Bao et al. |
| 2003/0225446 A1 | 12/2003 | Hartley |
| 2004/0016997 A1 | 1/2004 | Ushio |

(56) References Cited

U.S. PATENT DOCUMENTS

| | | |
|---|---|---|
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1* | 5/2004 | Eton ............ A61F 2/07 623/1.13 |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1* | 2/2006 | Evans ............ A61F 2/07 623/1.21 |
| 2006/0074481 A1 | 4/2006 | Vardi et al. |
| 2006/0095124 A1 | 5/2006 | Benz et al. |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0212112 A1* | 9/2006 | Evans ............ A61F 2/07 623/1.25 |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162109 A1 | 7/2007 | Davila et al. |
| 2007/0208416 A1 | 9/2007 | Burpee et al. |
| 2007/0276477 A1* | 11/2007 | Lee ............ A61L 31/10 623/1.44 |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0198267 A1 | 8/2009 | Evans et al. |
| 2009/0209855 A1 | 8/2009 | Drilling et al. |
| 2009/0216125 A1 | 8/2009 | Lenker |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0106087 A1 | 4/2010 | Evans et al. |
| 2010/0217383 A1 | 8/2010 | Leonhardt et al. |
| 2012/0016456 A1 | 1/2012 | Herbowy et al. |
| 2012/0046684 A1 | 2/2012 | Evans et al. |
| 2012/0184982 A1 | 7/2012 | Herbowy et al. |
| 2012/0259406 A1 | 10/2012 | Schreck et al. |
| 2014/0277385 A1 | 9/2014 | Bankert et al. |

FOREIGN PATENT DOCUMENTS

| | | |
|---|---|---|
| EP | 95302708.3 | 11/1995 |
| EP | 1325717 | 7/2003 |
| EP | 1903985 | 4/2008 |
| FR | 2834199 A1 | 7/2003 |
| JP | H04-322665 A | 11/1992 |
| JP | 2003-525692 | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | WO-97/17912 A1 | 5/1997 |
| WO | 97/19653 | 6/1997 |
| WO | 98/53761 A1 | 12/1998 |
| WO | WO-99/00073 A1 | 1/1999 |
| WO | WO-99/44539 A2 | 9/1999 |
| WO | 00/29060 A2 | 5/2000 |
| WO | WO 00/51522 A1 | 9/2000 |
| WO | WO 01/21108 A1 | 3/2001 |
| WO | WO 01/66038 A2 | 9/2001 |
| WO | 02/078569 A2 | 10/2002 |
| WO | 02/083038 A2 | 10/2002 |
| WO | WO 02/102282 A1 | 12/2002 |
| WO | 03/007785 A2 | 1/2003 |
| WO | 03/032869 A1 | 4/2003 |
| WO | 03/037222 A2 | 5/2003 |
| WO | 03/053288 A1 | 7/2003 |
| WO | WO-03/103513 A1 | 12/2003 |
| WO | 2004/004603 A1 | 1/2004 |
| WO | 2004/026183 A2 | 4/2004 |
| WO | 2004/026183 A3 | 4/2004 |
| WO | 2004/037116 A2 | 5/2004 |
| WO | 2004/037116 A3 | 5/2004 |
| WO | WO 04/045393 A2 | 6/2004 |
| WO | 2006/012567 A2 | 2/2006 |
| WO | 2006/116725 A2 | 11/2006 |
| WO | 2007/008600 A2 | 1/2007 |
| WO | WO-2007/142916 A2 | 12/2007 |

OTHER PUBLICATIONS

Chinese Application No. 201080065043.8, Notice of Grant for Invention, dated Apr. 25, 2016, 4 pages.
European Office Action dated Aug. 8, 2018, from application No. 10841580.3.
Examination report of EP Application No. 06751879.5, dated Mar. 24, 2014, 5 pages.
Examination Report of European App. 0375880.7, dated Feb. 22, 2013.
Examination Report of European Application No. 03754880.7, dated Jun. 29, 2012, 4 pages.
Examination Report of European Patent Application 03754880.7, dated Dec. 16, 2010.
Examination Report of European Patent Application 03754880.7, dated Dec. 22, 2011.
Examination Report of Japanese Patent Application No. 2007/522822, dated Feb. 8, 2011.
Examination Report of Japanese Patent Application No. 2008-5477019, dated Jul. 22, 2013.
Examination Report of Japanese Patent Application No. 2011-506487, dated Jun. 11, 2013.
Examination Report of Japanese Patent Application No. 2011-506487, dated May 7, 2014.
Extended European Search Report of Application No. 11180827.5, dated Jan. 30, 2012, 6 pages.
First Office Action of Chinese Application No. 201080065043.8, dated Aug. 1, 2014 (22 pages).
International Preliminary Report on Patentability and Written Opinion of The International Searching Authority, Issued in PCT/US2010/061621 dated Jul. 12, 2012, 7 pages.
International Search Report and Written Opinion of PCT Application No. PCT/US2009/046310, dated Jul. 29, 2009, 9 pages total.
Japanese Office Action dated Dec. 5, 2017, from application No. 2012-547147.
Notice of Reason for Refusal of Japanese Application No. 2012-547147, dated Sep. 8, 2015 (5 pages).
Notice of Reason of Refusal of Japanese Application No. 2012-547147, dated Sep. 16, 2014, 5 pages.

(56) References Cited

OTHER PUBLICATIONS

Official Action for Japanese Patent Application No. 2008-547709, dated Oct. 30, 2012.
Search report of corresponding PCT/US2014/021928, dated May 20, 2014, 8 pages.
Second Office Action of Chinese Application No. 201080065043.8, dated May 5, 2015 (16 pages).
U.S. Final Office Action dated Aug. 19, 2013, from U.S. Appl. No. 12/966,852.
U.S. Final Office Action dated Dec. 10, 2015, from U.S. Appl. No. 12/966,852.
U.S. Final Office Action dated Dec. 17, 2014, from U.S. Appl. No. 12/966,852.
U.S. Non-final Office Action dated Jun. 19, 2015, from U.S. Appl. No. 12/966,852.
U.S. Non-final Office Action dated Mar. 14, 2014, from U.S. Appl. No. 12/966,852.
U.S. Non-final Office Action dated Oct. 4, 2012, from U.S. Appl. No. 12/966,852.
U.S. Appl. No. 61/052,059, filed May 9, 2008; first named inventor: Gwendolyn A. Watanabe.
Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.
Journal of Endovascular Therapy; Apr. 2000; pp. 111, 114, 132-140; vol. 7' No. 2; International Society of Endovascular Specialists; Phoenix, AZ.
William Tanski, Mark Fillinger. Outcomes of original and low-permeability Gore Excluder endoprosthesis for endovascular abdominal aortic aneurysm repair. Journal of Vascular Surgery, Feb. 2007. p. 243-249.
Susan M. Trocciola et al. The development of ertdotension is associated with increased transmission of pressure and serous components in porous expanded polytetrafluoroethyiene stent-grads: Characterization using a canine model. Journal of Vascular Surgery Jan. 2006, p. 109-116.
Shan-e-ali Haider et al. Sac behavior after aneurysm treatment with the Gore Excluder low-permeability aortic endoprosthesis: 12-month comparison to the original Excluder de-vice. Journal of Vascular Surgery. vol. 44, No. 4. 694-700. Oct. 2006.
International Search Report of PCT/US 06/16403, dated Aug. 7, 2007. 2 pages.
International Search Report and Written Opinion of PCT Application No. PCT/US2006/062257, dated Jan. 18, 2008. 7 pages total.
International Search Report and Written Opinion of PCT Application No. PCT/US07/69671, dated Jul. 7, 2008, 9 paces.
International Search Report and Written Opinion of PCT Application No. PCT/US09/34136, D dated Apr. 8, 2009, 16 pages total.
U.S. Appl. No. 12/371,087, filed Feb. 13, 2009, first named inventor: K.T. Venkateswara Rao.
International Search Report and Written Opinion of Pot Application No. PCT/US09/41718, dated Jun. 22, 2009, 23 pages total.
Supplementary European Search Report and Search Opinion of EP Patent Application No. 05773726, dated Apr. 23, 2010, 6 pages total.
International Search Report and the Written Opinion of the International Searching Authority, Issued in PCT/US2012/032612 dated Jul. 25,2012, 13 pages.
International Search Report of the International Searching Authority for Application No. PCT/US2012/021878, dated May 23, 2012, 4 pges.
Written Opinion, including the search, of the International Searching Authority for Application No. PCT/US2012/021878, dated May 23, 2012, 9 pages.
Extended European search report of corresponding EP Application No. 06751879.5, dated Apr. 16, 2013, 9 pages.
European Search Report and Search Opinion of EP Patent Application No. 06774540.6, dated Mar. 30, 2010, 6 pages total.
EP report, dated Nov. 7, 2013, of corresponding EP Application No. 09733719.0.
Search report dated Oct. 17, 2013 of corresponding PCT/US2012/032612.
International Preliminary Report on Patentability PCT/US2012/021878 dated Aug. 1, 2013.
Report of European Patent Application No. 06850439.8 dated May 15, 2013.
Examiniation report for JP Application No. 2008-547709 dated Dec. 13, 2011.
International Search Report and Written Opinion of PCT Application No. PCT /US2009/046308, dated Nov. 17, 2009, 12 pages total.
Examination Report of corresponding Japanese Application No. 2011-512667, dated Jun. 18, 2013.
U.S. Appl. No. 60/855,889, filed Oct. 31, 2016; first named inventor: Steven L. Herbowy.
U.S. Appl. No. 61/052,059, filed May 9, 2008; first named inventor: Gwendolym A. Watanabe.
Carmi et al., "Endovascular stent-graft adapted to the endoluminal environment: prototype of a new endoluminal approach," J Endovasc Ther. Jun. 2002;9(3):380-381.
Donayre et al., :Fillable Endovascular Aneurysm Repair: An Early Look at a Next Generation EVAR Technology That May Address Some Current Limitations and Improve Clinical Outcomes, *Endovascular Today*, 64-66 (Jan. 2009).
Gilling-Smith, "Stent Graft Migration After Endovascular Aneurysm Repair," presented at 25th International Charing Cross Symposium, Apr. 13, 2003 [Power Point Presentation and Transcript], 56 pages total.
PCT International Search Report and Written Opinion dated Feb. 28, 2011 for PCT Application No. PCT/US2010/61621.

\* cited by examiner

Section A-A

Section A-A

Section B-B

FILLING STRUCTURE FOR A GRAFT SYSTEM AND METHODS OF USE

CROSS-REFERENCES TO RELATED APPLICATIONS

The present application is a Continuation of U.S. non-provisional application Ser. No. 12/966,852, filed Dec. 13, 2010, which of, and claims the benefit of U.S. Provisional Patent Application No. 61/291,279 filed Dec. 30, 2009, the entire contents of each of which are incorporated herein by reference.

BACKGROUND OF THE INVENTION

1. Field of the Invention

The present invention relates generally to medical systems and methods for treatment. More particularly, the present invention relates to apparatus and methods for treating aneurysms.

Previous patent applications have described an approach to repairing an aneurysm by introducing a filling structure into the aneurysm, supporting the structure with a support structure, and filling the filling structure with a hardenable material that fills the aneurysm sac. Removing the support structure leaves a lumen for blood flow, and the hardenable material fills the sac and prevents blood pressure from enlarging it further.

Once it is placed into service, the filling structure experiences pulsatile pressure, and by design shields the aneurysm from most of this pressure. As a result, the aneurysm itself may change shape by reabsorption of thrombus between the filling structure and the artery wall, and shrinkage or remodeling of the artery wall itself. This may result in reduced pressure on the exterior of the filling structure. In some designs this may cause the inner lumen of the filling structure to grow through time-dependent elastic deformation or creep. It is desirable to prevent this change in the inner lumen as the aneurysm changes shape.

Aneurysms can occur in a range of shapes and sizes depending on the individual anatomy of the affected artery, the length of time it took to detect the aneurysm, blood pressure, and other factors. As a result, structures designed to repair aneurysms by filling the aneurism sac must either be designed to be effective across a range of sac shapes and sizes, or they must be supplied in multiple stock sizes, or they must be custom-made for a specific anatomy. Sometimes, the structures may have a combination of the aforementioned properties.

A promising class of intraluminal aneurysm repair devices employs a double walled filling structure to fill the aneurysm sac while maintaining a lumen for continued blood flow in the artery. In order to accommodate a range of aneurysm sizes, the double walled filling structure may be chosen such that it is capable of expanding to at least the size of the sac in all parts of the aneurysm. This obviates the need to make a custom version of the device for each aneurysm, and instead allows the surgeon to choose among a limited number of stock sized devices. In this case the filling structure is selected to be at least as large as the sac to be filled. Some embodiments may have an elastic outer wall that expands and conforms to the inner aneurysm wall, while other filling structures use a substantially inelastic outer wall that is thin and flexible so that as the filling structure is filled, the outer wall expands partially to completely fill the sac, and any remaining capacity takes the form of wrinkles or pleats in the outer wall of the filling structure. An advantage of the elastic outer wall is the potential absence of wrinkles, but a drawback is that an elastic outer wall will not conform exactly to abrupt changes in curvature of the sac.

When the device is deployed and filled with hardened filling medium, pressure on the aneurysm wall is relieved. Over time, thrombus in the aneurysm is reabsorbed and the aneurysm wall slackens, relieving counterpressure on the filling structure. Therefore, the filling structure and filling medium needs to be stiff enough that its internal lumen does not change shape as this happens. Discontinuities in the filling medium caused by wrinkles and pleats on the walls of the filling structure reduce the strength of the filled structure. It would be advantageous to have a filling structure that can be filled in such a way that no internal wrinkles remain in some of its parts. It would also be advantageous to have a filling structure that is strong enough to resist creep even in the absence of an uninterrupted fill, yet still be thin enough to be percutaneously deliverable through the vasculature, which typically requires a 14 Fr or less device.

In addition, it would also be desirable to have a filling medium with a chemistry that also adheres to walls of the filling structure during or after curing, so that the in-situ formed device can withstand the biomechanical loads and accommodate long-term remodeling of the aneurysm. This can be accomplished through additives thereby modifying the chemistry of the filling medium or modifying the chemistry or coating the inner layers of the filling structure so that filling medium adheres to the filling structure as the device forms in-situ.

In order to avoid device migration and leakage, it is also desirable that the device, when filled with hardened filling material, conform as closely as possible to the shape of the aneurysm at its proximal and distal ends. It is also desirable to provide means by which the filling structure may be made to conform closely to the necks of the aneurysm, while being made of a thin, inelastic material. It is also desirable to resist creep deformation and remodeling caused by the pulsatile pressure of blood against the device.

2. Description of the Background Art

U.S. Patent Publication No. 2006/0025853 describes a double-walled filling structure for treating aortic and other aneurysms. Copending, commonly owned U.S. Patent Publication No. 2006/0212112, describes the use of liners and extenders to anchor and seal such double-walled filling structures within the aorta. The full disclosures of both these publications are incorporated herein by reference. PCT Publication No. WO 01/21108 describes expandable implants attached to a central graft for filling aortic aneurysms. See also U.S. Pat. Nos. 5,330,528; 5,534,024, 5,843, 160; 6,168,592; 6,190,402; 6,312,462; 6,312,463; U.S. Patent Publications 2002/0045848; 2003/0014075; 2004/0204755; 2005/0004660; and PCT Publication No. WO 02/102282.

BRIEF SUMMARY OF THE INVENTION

In a first aspect of the present invention, a double-walled filling structure comprises a thin, flexible, non-porous and biocompatible outer material that prevents movement of fluids across its boundary and that is flexible enough to fill and conform to the irregular contours of the aneurysm wall. An inner lumen of the filling structure may be made of the same or a different material selected and oriented so as to have high resistance to circumferential creep and elastic deflection. The inner lumen may be reinforced by including a reinforcing member including fibers, wires, strips, or a sleeve oriented circumferentially so as to improve resistance to hoop stresses. The inner lumen may also be reinforced by the use of multiple layers of material. The inner lumen may be inserted into a tubular mesh or membrane of metal, polymer, or fibers in order to provide resistance against creep. If the inner lumen is tapered or contoured to provide a gradual change in diameter from one end to the other, the reinforcing lumen may also be tapered to match the lumen taper.

In a second aspect of the present invention, the inner lumen of the filling structure is constructed of a material with thickness and/or composition chosen to be capable of withstanding the maximum pulsatile pressure exerted by blood flow, without undergoing creep or significant elastic deformation. It is generally desirable to minimize thickness of the filling structure, so a variation on this aspect is to employ materials with anisotropic stress properties oriented and processed so as to have greatest strength in the circumferential direction. An example of such a material is expanded polytetrafluoroethylene, or ePTFE, which is typically stretched in one direction and may also be calendared to reduce its thickness and decrease its porosity. The ePTFE sheet exhibits anisotropic modulus with greatest value in the pre-stress axis, and also exhibits a strain hardening property in which the modulus increases with deformation along the axis of pre-stress. Thus by constructing the inner lumen of ePTFE, with a pre-stress axis oriented in the circumferential direction, it is possible to resist creep caused by blood pressure. Other materials may be employed in this capacity as well, provided they have sufficient strength in at least one axis, and are biocompatible and impervious to fluids.

A third aspect of the present invention involves attaching a support structure to the inside of the inner lumen of the filling structure. The internal support frame (endoframe) may be made of a biocompatible superelastic material such as Nickel-Titanium alloy (for example Nitinol), and may be used to support the inner lumen of the filling structure while it is being filled with hardenable material. The inner lumen of the filling structure may be contoured so that it matches the diameter of the endoframe at every position along its length to avoid wrinkles. By attaching the lumen to the frame at several points, the frame provides additional creep resistance to the lumen. This may be involve suturing, heat staking, solvent welding, or other methods well known in the art for attaching dissimilar materials to each other. Alternatively, the internal reinforcing elements may be made from balloon-expandable materials like stainless steel, cobalt-chromium alloys, etc. Ring shaped stiffeners may be sintered to either the outside or the inside of the inner lumen of the filling structure to provide support. In this case, the frame may comprise a set of such rings. The rings may be made of a biocompatible metal or polymer. The rings may be shaped such that they are compressible and readily expandable in situ, for example by forming each ring from an undulating or zigzag pattern.

In a fourth aspect of the present invention a reinforcing tube surrounds an inner lumen of a filling structure to provide additional reinforcement. This tube may be made of the same material as the inner lumen, or it may differ. Because the reinforcing tube does not contact blood or tissue, its biocompatibility requirements are lessened. The reinforcing tube may be of a continuous material, or it may be a mesh attached to the inner lumen by one of several methods well known in the art, including for example suturing, heat staking, solvent welding, ultrasonic welding, or adhesives. The tube material is chosen to have strength in the circumferential direction that, in combination with the strength provided by the inner lumen, resists creep caused by the peaks in blood pressure. Using Laplace's law:

$$\text{hoop stress}=\text{pressure}*\text{vessel radius}/\text{wall thickness}.$$

Using typical values for mean blood pressure=100 mmHg (healthy 80/120 mm Hg), radius R=7 mm (2-14 mm rounds to treat a 26 mm aorta), and assuming wall thickness of 150 microns, the typical stresses are about 600 MPa. Maximum stress is about 1100 MPa, and minimum hoop stress is estimated to be about 300 MPa.

In another aspect of the present invention, the filling medium may be modified through additives/covalent bonding so that it adheres to the walls of the filling structure and keeps the device intact and accommodates remodeling.

In still another aspect of the present invention, the inner walls of the filling structure may be modified through additives, coatings and covalent bonding so that the filling medium adheres to the filling structure and maintains the shape of the device.

In yet another aspect of the present invention, the filling structure includes two or more coaxial compartments, the inner of which is a hollow cylinder surrounding the inner lumen, and the outer of which is shaped to fill the aneurysm and conform to the irregular contours of the aneurysm wall. The inner compartment may be in fluid communication with the outer compartment. The inner and outer compartments may have separate fill ports, or a valve or flap may be provided to direct a flow of filling material first to one region, and then to the other region. The filling material is introduced to the inner region, and may flow to the outer region when the inner region fills, thereby providing a continuous layer of hardening medium surrounding the blood lumens of the filling structure. This results in the inner region being completely filled with a hollow cylinder of hardened filling medium reinforced by the inner and middle layers of the filling structure itself, preventing radial expansion. In addition, the inner compartment is sized such that it may be fully expanded without wrinkles while the outer compartment is sized to fill a wide range of aneurysm geometries that may be encountered and therefore may be of an elastic material, or of a flexible, substantially inelastic material such as PTFE or ePTFE that is large enough to fill a range of aneurysm cavities. In the latter case there may be wrinkles in the outer section of the filling structure after filling depending on the shape, size and pathophysiology of the aneurysm. These wrinkles may interrupt the structure of the hardened filling medium so that it may be broken into two or more sub-volumes, inhibiting its strength and providing room to depressurize and allow for re-modeling as part of the healing mechanism of the aneurysm.

The filling medium delivered to the inner region may be selected to have material properties that enhance its resistance to pulsatile pressure or creep. For example, the inner region material may be a Polyethylene Glycol (PEG)-based Hydrogel with a higher bulk modulus than the material delivered to the outer region. A harder material in the inner compartment dampens pulsatile forces and a softer material in the outer compartment allows ease of shaping and remodeling.

Similarly, the material targeted to the outer region may for example be selected to have lower viscosity before hardening so it fills the sac more evenly, a different hardening time, or the ability to bond with the wall of the filling structure. This may be achieved for example through chemical/covalent bonding by adding reactive functional groups to either the hydrogel or the inner wall of the filling structure or both. Hydrogen bonding may be preferentially used to create attachment of hydrogel to the inner surface of the filling structure. This may entail imparting donor hydrogen atoms and acceptor entity atoms in either the hydrogel or the wall of the filling structure or both. Physical adhesive/cohesive forces may be used to attach hydrogel to the inner surface at various pre-determined locations on the interface. The inner surface of the filling structure's outer wall may be modified by surface derivitization or by lamination to allow the filling material to bonds to it to improve overall strength.

In still another aspect of the invention, the filling structure's outer surface is coated with substances that promote the growth of epithelium on the outer surface, thus creating an enclosure around the filling structure that serves to maintain containment pressure over time. This approach may be combined with other approaches described herein to add strength.

In another aspect of the present invention, a method for treating an aneurysm comprises providing a double-walled filling structure having an outer wall and an inner wall, and positioning the double-walled filling structure adjacent the aneurysm. The filling structure is filled with a hardenable fluid filling medium so that the outer wall conforms to an inside surface of the aneurysm and the inner wall forms a generally tubular lumen to permit blood flow therethrough. The lumen is constrained from creeping or elastically expanding due to the blood flow through the lumen.

The constraining step may comprise providing a reinforcing layer disposed at least partially around the tubular lumen, or filling a compartment disposed at least partially around the tubular lumen with the hardenable fluid filling medium.

These and other embodiments are described in further detail in the following description related to the appended drawing figures.

DETAILED DESCRIPTION OF THE INVENTION

Figure 1:
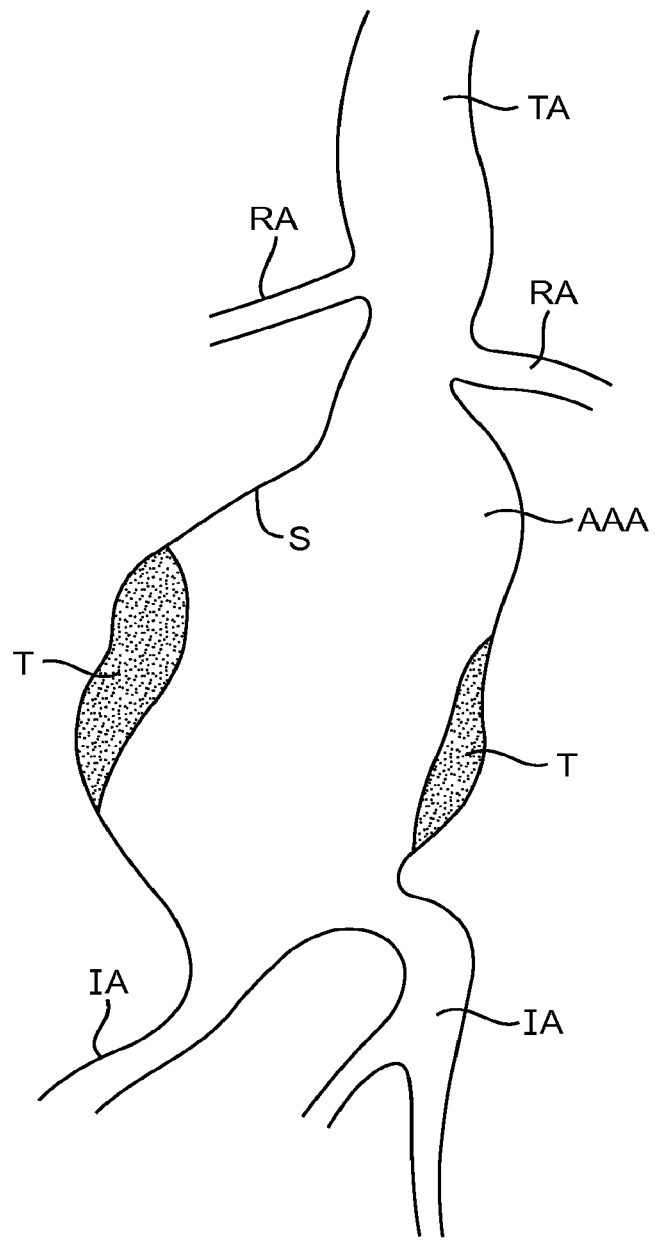
FIG. 1 illustrates the anatomy of an infrarenal abdominal aortic aneurysm.

Referring to FIG. 1, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 2:
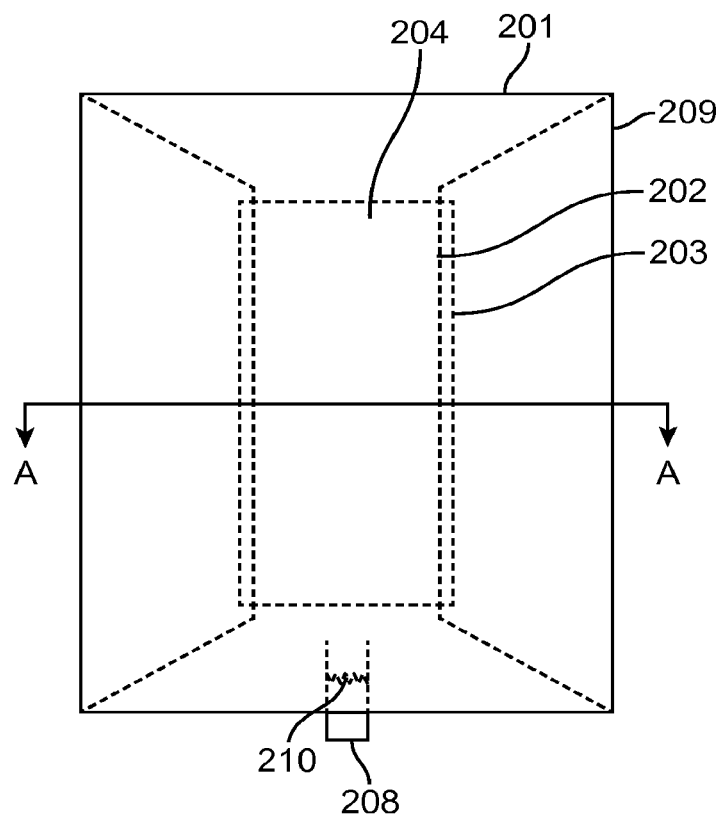
FIG. 2 illustrates a filling structure comprising a multi-layer reinforced inner lumen.
Figure 2:
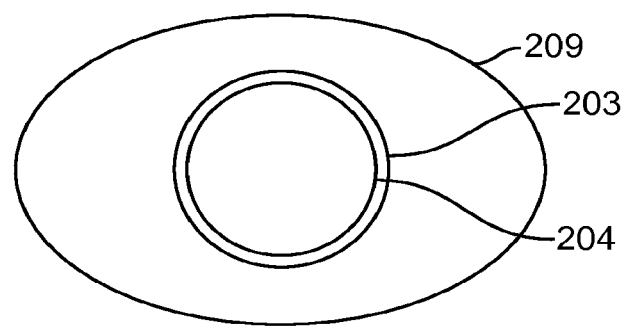

FIG. 2 illustrates a filling structure 201 embodying aspects of the invention. Filling structure 201 comprises central lumen 204 defined by luminal wall 202, outer wall 209, and reinforcing sleeve 203. Fill tube 208 is attached to a cannula during placement of the device, and allows hardenable filling material to enter the interior volume of the filling structure, then seals itself to prevent backflow of filling material when the cannula is removed. Fill tube 208 may comprise a tear line 210 created by a partial perforation or notched edges. The tear line allows part or the entire exterior portion of the fill tube to be removed when the fill cannula is removed so that none of the fill tube protrudes beyond the filling structure once the filling structure is placed. This prevents contact between the fill tube and the artery wall, reducing the risk of thrombosis.

Still referring to FIG. 2, reinforcing sleeve 203 may be laminated, welded, sewn, or adhesively attached to central lumen 204, or may be a separate sleeve that is placed over central lumen 204 during the assembly process. Both reinforcing sleeve 203 and central lumen 204 may vary in diameter in order to conform more closely to the natural diameter of the target artery, particularly at the ends. This may afford superior sealing by matching the diameter of the filling structure more closely to the diameter of the neck of the aneurysm.

Figure 3:
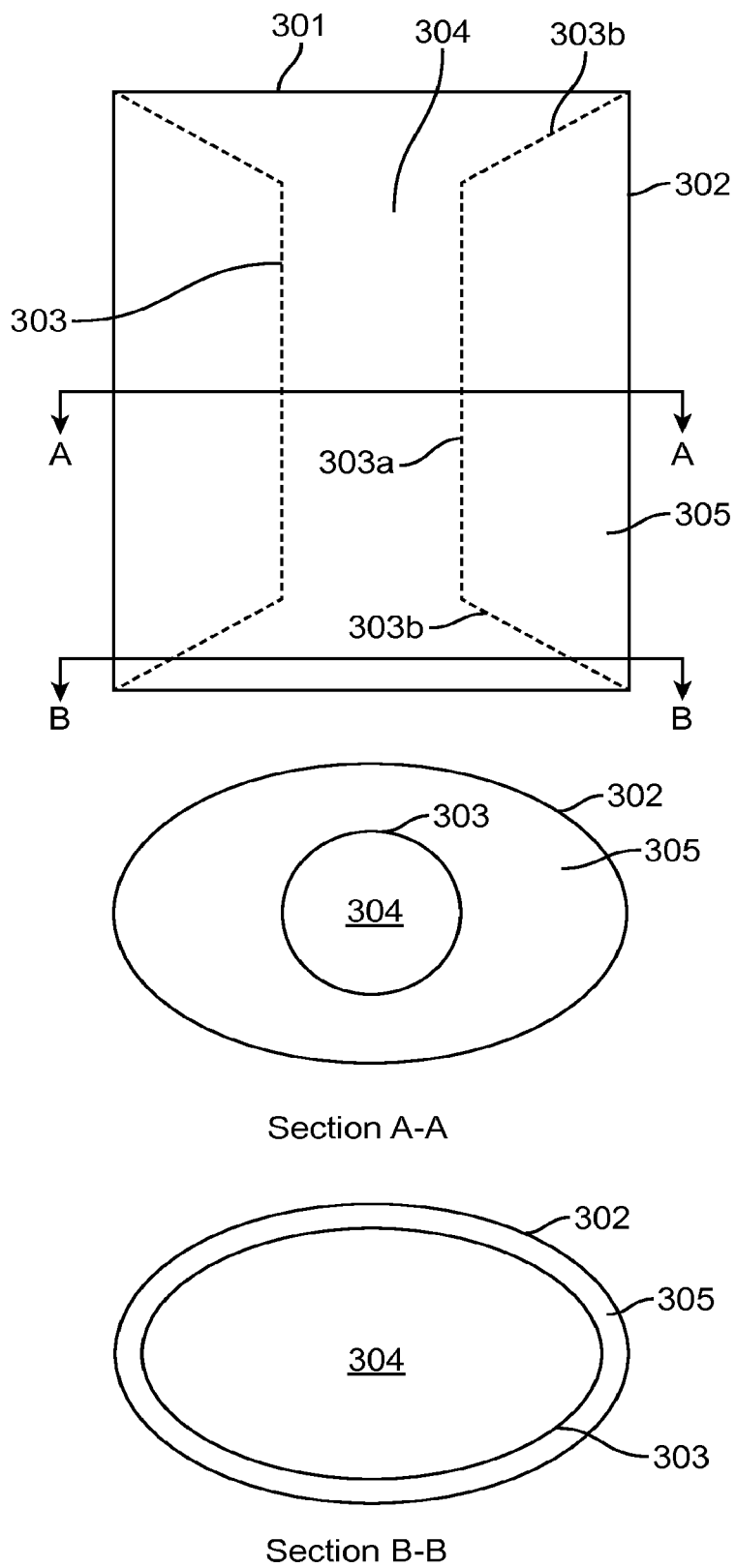
FIG. 3 illustrates a filling structure comprising an inner lumen with tapered ends.

As shown in FIG. 3, a filling structure 301 may be constructed such that inner lumen 303 varies in diameter over the length of the filling structure in order to increase filled volume 305 and improve sealing against one or more necks of the aneurysm. In one aspect, the filling structure 301 has an exterior wall 302 and a lumen 303. The lumen 303 has a larger diameter 304 at each end than at a point therebetween, and may comprise a cylindrical middle portion 303a with one or more conical end portions 303b. The slope of the shoulder of conical end portions 303b may be chosen to control the shape of filling structure 301 after it is filled. Choosing a maximum diameter of conical section 303b that is close to the outside diameter of the filling structure results in a more circular cross-section, while a smaller maximum diameter relative to the outside diameter of filling structure 301 results in an oval or eye-shaped cross-section. Other taper profiles for the inner lumen may be selected; for example it is possible to use a parabolic or hyperbolic profile to provide a continuous transition from one inner diameter to another, which may reduce turbulent flow in the lumen. Note that the foregoing description is for exemplary purposes and is not meant to exclude other diameter profiles.

Figure 4:
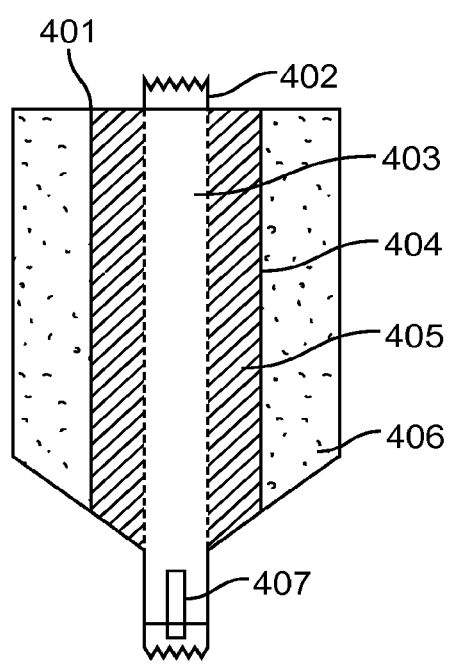
FIG. 4 illustrates a filling structure comprising multiple compartments.

FIG. 4 illustrates a filling structure 401 comprising at least two filling compartments. Endoframe 402 may be used to support the filling structure while it is being filled, maintaining a diameter of interior lumen 403. Inner compartment 404 may be connected directly to a fill valve 407 such that filling material enters compartment 404 forming an inner polymer jacket 405 before flowing to outer compartment 406. In this aspect the two compartments may be in fluid communication with each other, optionally with a restriction between the two compartments such that the viscosity of the filling medium inflates the inner compartment fully before filling the outer compartment. U.S. patent application Ser. No. 12/429,474 discloses various delivery system configurations and methods for delivering and deploying a filling structure that may be used for any of the filling structures disclosed herein, the entire contents of which are incorporated herein by reference.

In an alternate aspect, inner compartment 404 may be separated from outer compartment 406 and each compartment may have a separate fill valve similar to fill valve 407. In this case valve 407 communicates with the inner compartment and another fill valve (not shown) communicates with the outer compartment. This permits the use of two different filling media, each with potentially different material properties. For example, the inner compartment-filling medium may be selected for a fast cure time to allow rapid removal of the endoframe 402, or for a larger bulk modulus to provide enhanced resistance to pulsatile pressure. The outer compartment-filling medium may for example be selected for enhanced adhesion to an inner wall of filling structure 401. Separate fill valves also allow the compartments to be filled in a controlled order. In one aspect, the inner compartment is filled before the outer compartment to allow the inner compartment to be fully filled, providing a solid structure for resisting pulsatile pressure. The outer compartment is then filled sufficiently to fill the aneurysm sac without overloading the artery wall.

Figure 5A:
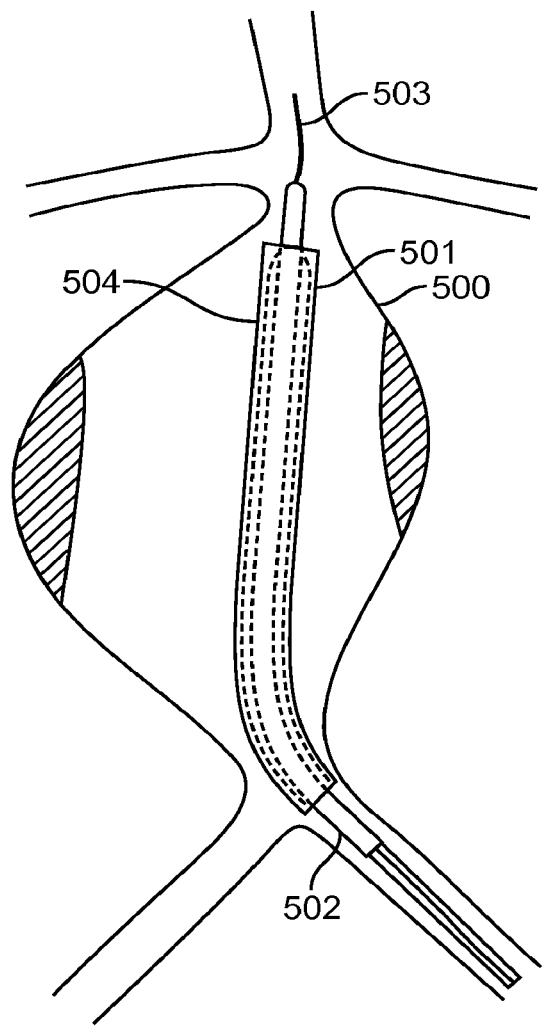
FIGS. 5A-5D illustrate an exemplary method of deploying a filling structure in an aneurysm.

Referring now to FIG. 5a, we describe an exemplary method of placing and filling a multi-partition filling structure in an aneurysm 500. Furled filling structure 501 is introduced to the aneurysm on guidewire 503 and cannula 502. Sheath 504 is withdrawn to release filling structure 501. Cannula 502 contains guidewire 503 as well as one or more optional lumens (not illustrated) for filling the filling structure compartments, and possibly for introducing an endoframe and expansion balloon, as well as lines permitting detachment of the filling structure and other components from the cannula for deployment.

Figure 5B:
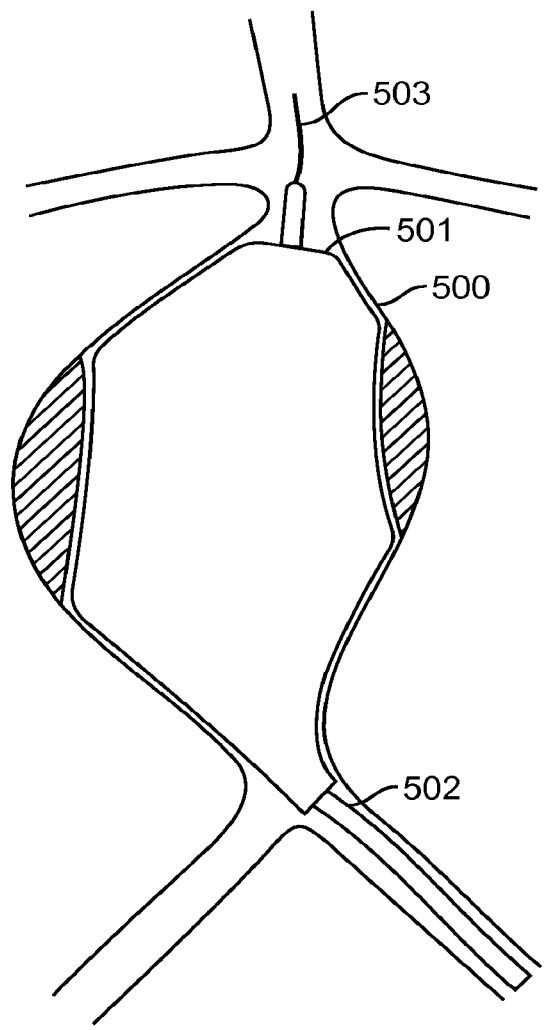

Continuing to FIG. 5b, the unfurled filling structure may be unfurled completely by filling with a solution containing contrast agent, saline, combinations thereof, as well as other fluids. This is advantageous since the walls of the filling structure may stick against adjacent walls, especially after terminal sterilization and storage. Once unfurled, the volume of solution required to unfurl may be used as an estimate of the volume of hydrogel mix to introduce in order to fill the aneurysm sac completely without overpressure on the wall.

Figure 5C:
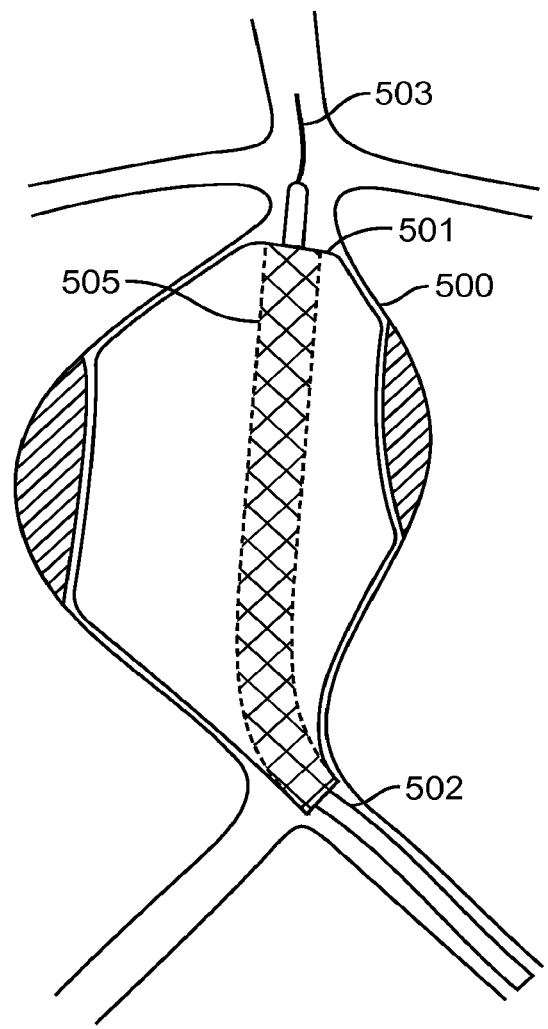

Continuing to FIG. 5c, endoframe 505 may be introduced into the inner lumen of filling structure 501 to support the inner lumen during the hydrogel filling step. Endoframe 505 may be self-expanding, or may be expanded by an expandable member such as a balloon (not illustrated) introduced via cannula 502. Endoframe 505 may be withdrawn after the filling step, or may be left in place indefinitely.

Figure 5D:
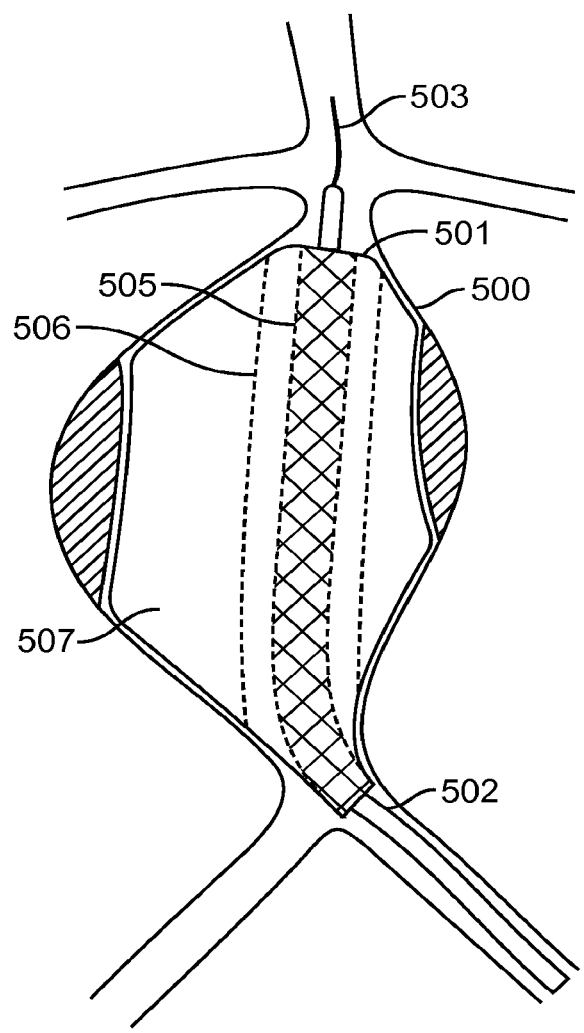

Continuing to FIG. 5d, uncured liquid hydrogel is introduced through cannula 502 into inner partition 506 of filling structure 501. In one aspect, inner partition 506 may be in restricted fluid communication with outer partition 507 of filling structure 501. In this case, once inner partition 506 is filled, hydrogel flows to outer partition 507 via a passageway. The hydrogel's viscosity in combination with the cross-section area of the passageway causes inner partition 506 to stay inflated while outer partition 507 fills with the remaining volume of hydrogel until filling structure 501 completely fills the aneurysm sac. In another aspect, inner partition 506 and outer partition 507 may be filled by independent filling tubes (not illustrated) in cannula 502. In this aspect, inner partition 506 is filled until a measured pressure of the hydrogel reaches a threshold pressure, or until a dispensed volume of hydrogel reaches a threshold volume indicating complete filling of inner partition 506. Then outer partition 507 is filled with the remaining volume of hydrogel as estimated in the pre-fill step described previously. Note that the filling structure may comprise more than two compartments, in which case the filling process continues until all compartments are properly and completely filled. Once the hydrogel cures—preferably in less than ten minutes, and more preferably in less than five minutes, and even more preferably in less than about 4 minutes, the filling tubes may be detached from the filling structure and the cannula and guidewire may be withdrawn. Note that this process may be conducted on two filling structures simultaneously, with one filling structure inserted through each iliac artery. Filling of the filling structure may be performed with the endoframe expanded fully or partially, or the endoframe may be unexpanded. Additionally, the expandable member may be partially or fully expanded, or unexpanded during the filling procedure. Filling may also be visualized using fluoroscopy, ultrasound, or other methods in order to ensure that the filling structure properly expands and fills the aneurismal space.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A system for treating an aneurysm in a patient, said system comprising:
   a double-walled filling structure having an outer wall and an inner wall, wherein the outer wall and the inner wall define a fillable space, wherein the fillable space is adapted to be filled with a hardenable fluid filling medium such that when said filling structure is positioned across the aneurysm and filled with said hardenable fluid filling medium, said outer wall expands to conform to an inside surface of the aneurysm and said inner wall forms a tubular lumen to permit blood flow therethrough; and
   a reinforcing sheet having an interior surface and an exterior surface disposed over said inner wall such that the interior surface is in contact with the inner wall, wherein said reinforcing sheet is separate from said inner wall and is disposed within said fillable space, wherein the tubular lumen formed by said inner wall has an inner wall longitudinal length, and wherein said reinforcing sheet has a reinforcing sheet longitudinal length that is less than said inner wall longitudinal length and is adapted to prevent circumferential creep or elastic expansion of said tubular lumen after deployment.

2. The system of claim 1, wherein said reinforcing sheet comprises a metal, textile, membrane, or polymer mesh that surrounds a blood contacting layer defined by said inner wall so as to avoid contact with blood flowing through the tubular lumen formed by said inner wall.

3. The system of claim 1, wherein said reinforcing sheet comprises fibers or filaments disposed around said tubular lumen formed by said inner wall and oriented circumferentially so as to increase resistance to radial expansion.

4. The system of claim 3, wherein the fibers or filaments comprise a metal, a polymer, a membrane, or a textile.

5. The system of claim 1, wherein said reinforcing sheet comprises fibers or filaments disposed spirally around the tubular lumen formed by said inner wall and adapted to resist radial expansion of the inner wall of the lumen.

6. The system of claim 1, wherein said filling structure is configured so that the tubular lumen formed by said inner wall has proximal and distal ends, and wherein the proximal and distal ends are flared.

7. The system of claim 1, wherein said inner wall is conformable to a shape and diameter of an expanded endoframe as limited by the diameter of the reinforcing sheet during filling; and
   wherein said reinforcing sheet is attached to the inner wall.

8. The system of claim 1, wherein said separate reinforcing sheet is attached to the inner wall by one or more sutures.

9. The system of claim 1, wherein said reinforcing sheet is positioned between said inner wall and said outer wall.

10. The system of claim 1, wherein said reinforcing sheet occupies a space between said inner wall and said outer wall.

11. The system of claim 1, wherein said reinforcing sheet is made of a material having anisotropic stress properties oriented such that its greatest tensile strength is circumferential.

12. The system of claim 1, wherein a material of which the reinforcing sheet is formed surrounds the inner layer wall and is contiguous along a length of the reinforcing sheet.

13. The system of claim 1, wherein a material of which the reinforcing sheet is formed surrounds the inner layer wall with an uninterrupted continuous circumferential horizontal cross-section of the filling structure.

14. A system for treating an aneurysm in a patient, said system comprising:

an expandable endoframe positionable across the aneurysm;

a first double-walled filling structure having a differential functional construct including a toroidal outer surface having a tubular inner lumen formed therethrough, wherein said expandable endoframe and said first double-walled filling structure are separate components, wherein said filling structure defines a fillable space fillable with a hardenable fluid filling medium such that when said filling structure is positioned across the aneurysm around said expanded endoframe and filled with said hardenable fluid filling medium, an outward facing wall surface conforms to an inside surface of the aneurysm and an inward facing wall surface forms said tubular inner lumen therethrough, wherein when expanded said expandable endoframe supports said inward facing wall forming said tubular lumen to permit blood flow therethrough, and a reinforcing sheet that is separate from said inward facing wall and is disposed within said fillable space and attached to the inward facing wall wherein the tubular inner lumen formed by said inward facing wall has an inward facing wall longitudinal length, and wherein said reinforcing sheet has a reinforcing sheet longitudinal length that is less than said inward facing wall longitudinal length such that said reinforcing sheet inhibits radial expansion of said inward facing wall forming said tubular lumen from expansion of said endoframe and due to creep or elastic expansion of said inward facing wall by outwardly directed mechanical forces from blood flow and long-term aneurysmal remodeling.

* * * * *